Figure 1A:
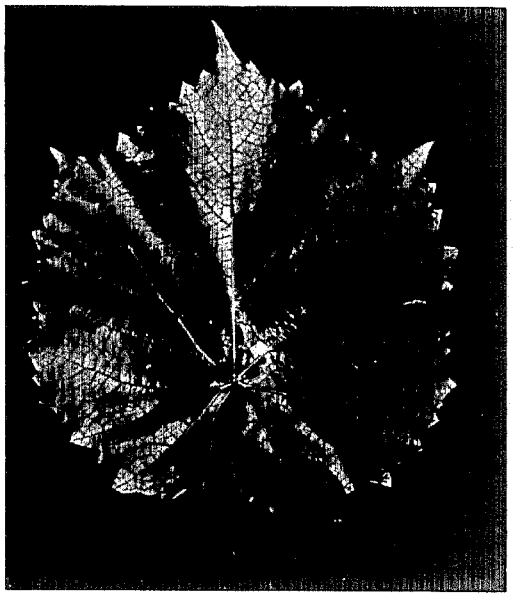

United States Patent [19]

Reisch et al.

[11] Patent Number: Plant 6,159

[45] Date of Patent: Apr. 26, 1988

[54] GRAPEVINE, "MELODY", NY 65.444.4

[75] Inventors: Bruce I. Reisch; Robert M. Pool, both of Geneva; John P. Watson, Phelps, all of N.Y.; John Einset, deceased, late of Geneva, N.Y., by Hjordis Einset, executrix

[73] Assignee: Cornell Research Foundation, Inc., Ithaca, N.Y.

[21] Appl. No.: 795,698

[22] Filed: Nov. 5, 1985

[51] Int. Cl.[4] ..... A01H 5/03

[52] U.S. Cl. ..... Plt./47

[58] Field of Search ..... Plt./47

[56] References Cited

PUBLICATIONS

New York State Fruit Testing Cooperative Assoc. Bulletin 1982–1983.

1986 New York State Fruit Testing Cooperative Assoc. Bulletin.

Eastern Grape Growers and Winery News, Oct./Nov. 1985.

Wine East, Nov./Dec. 1985.

Rochester Democrat and Chronicle, Sep. 20, 1985.

*Primary Examiner*—Robert E. Bagwill

*Attorney, Agent, or Firm*—Jones, Tullar & Cooper

[57] ABSTRACT

A new and distinct variety of grapevine named 'Melody', and tested as NY 65.444.4, which originated from seed produced by a hand pollinated cross of 'Seyval' (non-patented) and GW5 from New York (non-patented) is described. This new variety can be distinguished by its vinifera-type wine with varietal character, its resistance to powdery mildew infection and its adaptation to the climate of the grape growing regions of New York.

2 Drawing Sheets

SUMMARY

This invention is a new and distinct variety of grapevine, 'Melody', NY 65.444.4, from a cross of 'Seyval' and GW5 from New York, which can be distinguished by its vinifera-type wine with varietal character, its resistance to powdery mildew and its adaptation to the climate of the grape growing regions of New York.

ORIGIN

'Melody' was developed by a breeding program of the Department of Horticultural Sciences, Cornell University, New York State Agricultural Experiment Station, Geneva, N.Y. 'Melody' resulted from the cross of 'Seyval' with the New York selection, Geneva White 5 (GW 5)—itself a progeny of 'Pinot blanc'×'Ontario'. The cross was made in 1965 and the fruit were first described in 1969. It was propagated for further testing in 1972. 'Melody' has been known previously as NY 65.444.4.

DESCRIPTION

Own-rooted vines of 'Melody' are vigorous and productive. Annual cane pruning weights usually exceed 1.0 kg per vine on phylloxera (*Daktulosphaira vitifoliae* Fitch)—infested soils. At Geneva, these vines have produced more than 9.3 kg fruit/vine between 1982 and 1984. Though apt to be affected by site and management inputs, 'Melody' can be expected to be a highly productive cultivar in commercial plantings.

The vines are moderately winter hardy at Geneva, although occasional trunk injury has been observed. Following the test winter of 1980–1981, 'Melody' had 78% shootless nodes, while 'Concord', 'Horizon', 'Seyval', and 'Cayuga White', and 'Pinot' Chardonnay had 6, 30, 64, 68 and 98% shootless nodes, respectively. The level of winter hardiness of 'Melody' appears to be comparable to 'Seyval'.

Flowers are perfect and self-fertile with small pistils and bloom is late. The shouldered fruit clusters are medium-small by weight, well-filled to compact, and usually borne two clusters per shoot. Cluster thinning is not required, however, some late maturing crop is usually produced. Berries are medium-sized, spherical and range in color from light green to amber. The skin is resistant to cracking.

'Melody' ripens between September 25 and October 6 at Geneva. Most soluble solids have averaged 18.6° Brix (13 year mean) and post-fermentation titratable acidity was 8.4 g/liter (11 year mean). Wine was first made in 1970 and has consistently ranked high in taste panel scores. The wines have a neutral fruitiness with floral overtones and slight hints of herbaceousness. Fermentation at 10° C. has produced wines superior to those fermented at 15.6°–26.7° C.

Foliage and fruit are apparently resistant to powdery mildew and botrytis bunch rot (*Botrytis cinerea* Pers.) though slight symptoms of each have been observed in field plantings. Some downy mildew (*Plasmopara viticola* [Berk. and Curt.]) has been observed in some years on both foliage and fruit.

DESCRIPTION OF THE PHOTOGRAPHS

The accompanying photographs show typical specimens of the fruit and leaves of the new variety in color as nearly true as it is reasonably possible to make in a color illustration of this character.

Figure 1B:
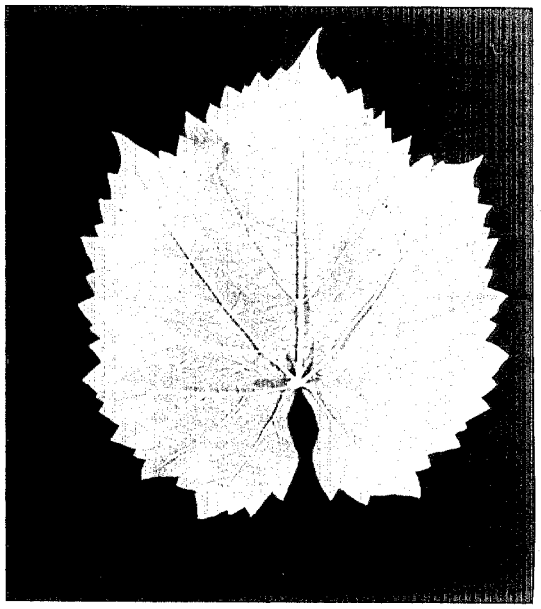
Figure 1C:
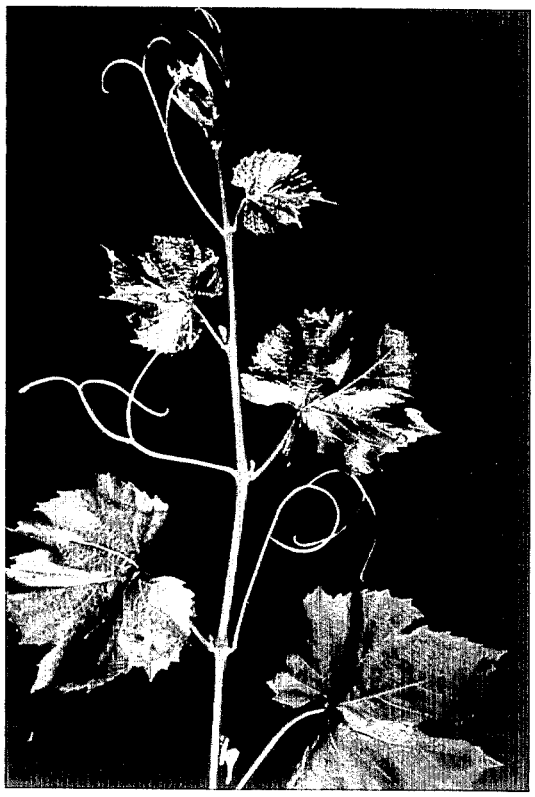
Figure 1D:
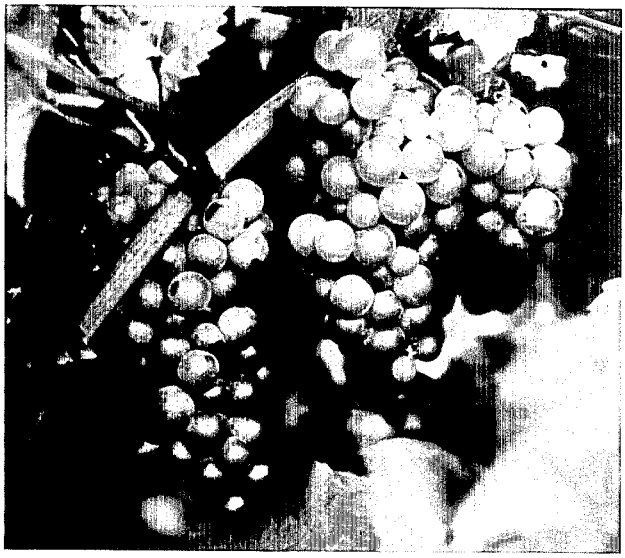

FIG. 1. A-mature leaf, upper surface, B-mature leaf, lower surface, C-young shoot and D-fruit clusters of 'Melody'.

The following is a detailed description of the pomological characteristics of the subject grapevine. Color terminology is in accordance with that of the "Royal Horticultural Society Colour Chart" published in 1966 by The Royal Horticultural Society of London, England.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

The descriptions reported herein are from specimens grown at Geneva, N.Y.

Vine: Vigorous, exceeding 1.0 kg cane prunings/vine/-year, upright in growth habit. Bud break follows 'Concord' by several days. The trunk is strong and sheds bark in long and wide longitudinal strips. Bark color ranges from greyed purple 183D to purple 79A (approximate).

Shoot tip: Curved, forming angles as small as 90° with the shoot, wooly downy to cobwebby indument. Tips have a white color with a faint rose margin. The first flat leaf is rust-brown and cobwebby.

Shoot: Inflorescences are usually borne at nodes 3 and 4 from the base, some lateral shoot production follows bloom. Tendrils are slender and wiry, and discontinuous along the shoot.

Mature leaves: 3-lobed, orbicular shape, with a slightly opened v-shaped petiolar sinus. The superior sinus is shallow and v-shaped. Upper surface is glabrous, flat, bullate and green (137B) in color. Lower surface of leaf is bullate, glabrous and green (138C) in color. Petioles are red 53B on a green 139C background.

Flowering: Approximately 10 days following Concord.

Clusters: Shouldered, medium-small, averaging 143 g per cluster over three years. Usually borne 2 per shoot on primary shoots, with some frequency of clusters occurring on secondary and lateral shoots, as well as from shoots arising from base buds. Clusters are medium-dense.

Fruit: Medium-sized and spherical in shape, fully seeded, maturing in early October at Geneva. The skin is tough and resistant to cracking and has a yellow-green color, 145C, with a light waxy bloom.

Productivity: Averaged 9.7 kg/vine (very productive) over 3 years.

Fruit analysis: 18.6° Brix (3 year average), 8.4 g/l post-fermentation titratable acidity (11 year average) and 3.13 pH (3 year average).

Wine character: Ranks very high, produces vinifera-style wine with neutral fruitiness, floral overtones and slight hints of herbaceousness. Consistently high ranking in 14 years of testing.

Isozyme analysis:

| | Phosphoglucose isomerase (GPI) Rf | | | | | |
|---|---|---|---|---|---|---|
| | 0.08 | 0.13 | 0.16 | 0.23 | 0.36 | 0.58 |
| Melody | + | + | + | | | + |
| Vignoles | + | + | | | + | + |
| Horizon | + | | | | | + |
| Vidal blanc | + | | | + | + | + |
| Seyval | + | | | | | + |
| Ontario | + | | | + | + | + |
| GW 5 | + | + | + | | | + |
| Pinot blanc | | | + | | | + |
| Aurore | + | | | + | + | + |
| Cayuga White | + | | | + | + | + |

| | Phosphoglucomutase (PGM) Rf | | |
|---|---|---|---|
| | 0.10 | 0.22 | 0.39 |
| Melody | + | + | + |
| Vignoles | + | + | + |
| Horizon | + | | + |
| Vidal blanc | + | + | + |
| Seyval | + | | + |
| Ontario | + | | + |
| GW 5 | + | + | + |
| Pinot blanc | | + | + |
| Aurore | + | + | + |
| Cayuga White | + | | + |

pg,7

We claim:

1. The new and distinct variety of grapevine herein described and illustrated and identified by the characteristics enumerated above.

* * * * *